(12) United States Patent
Schwarz et al.

(10) Patent No.: US 6,691,966 B1
(45) Date of Patent: Feb. 17, 2004

(54) HOLDING SYSTEM FOR ACCESSORY INSTRUMENTS, ESPECIALLY IN MINIMALLY INVASIVE SURGERY

(75) Inventors: Knut M. Schwarz, Tubingen (DE); Marc O. Schurr, Tubingen (DE); Gerhard F. Bues, Tubingen (DE)

(73) Assignee: Tuebingen Scientific Surgical Products, oHG, Tubingen (DE)

( * ) Notice: Subject to any disclaimer, the term of this patent is extended or adjusted under 35 U.S.C. 154(b) by 0 days.

(21) Appl. No.: 09/702,039

(22) Filed: Oct. 28, 2000

(30) Foreign Application Priority Data

Oct. 29, 1999 (DE) .......................................... 199 52 208
Mar. 17, 2000 (DE) .......................................... 100 13 146

(51) Int. Cl.⁷ ................................................. A61B 1/00

(52) U.S. Cl. ..................... 248/276.1; 248/324; 248/314; 248/288.31; 248/288.51

(58) Field of Search ................................ 248/324, 314, 248/276.1, 288.31, 288.51; 606/1; 403/83, 84, 87, 99

(56) References Cited

U.S. PATENT DOCUMENTS

| | | | | |
|---|---|---|---|---|
| 3,708,177 A | * | 1/1973 | Baermann | 148/103 |
| 4,336,946 A | * | 6/1982 | Wheeler | 277/529 |
| 5,405,344 A | * | 4/1995 | Williamson et al. | 606/1 |
| 5,419,522 A | * | 5/1995 | Luecke et al. | 248/288.51 |
| 5,803,642 A | | 9/1998 | Sassmannshausen | 403/90 |
| 5,868,509 A | * | 2/1999 | Crutcher | 401/7 |
| 5,918,844 A | * | 7/1999 | Ognier | 248/276.1 |
| 6,039,725 A | * | 3/2000 | Moenning et al. | 604/108 |
| 6,070,835 A | * | 6/2000 | Stillinger | 248/49 |
| 6,309,345 B1 | * | 10/2001 | Stelzer et al. | 600/106 |
| 6,328,748 B1 | * | 12/2001 | Hennig | 606/130 |

FOREIGN PATENT DOCUMENTS

| | | | |
|---|---|---|---|
| DE | 1 762 727 | 3/1958 | |
| DE | 88 00 450.9 | 7/1988 | ........... A61B/19/00 |
| DE | 43 31 277 C1 | 2/1995 | ........... A61B/17/02 |

* cited by examiner

Primary Examiner—Ramon O. Ramirez
Assistant Examiner—Jon Szumny
(74) Attorney, Agent, or Firm—William W. Jones

(57) ABSTRACT

A holding and positioning system for locating adjunct surgical accessory instruments relative to a patient's body during arthroscopic surgery.

3 Claims, 7 Drawing Sheets

HOLDING SYSTEM FOR ACCESSORY INSTRUMENTS, ESPECIALLY IN MINIMALLY INVASIVE SURGERY

TECHNICAL FIELD

The present invention relates to a holding system for surgical accessory instruments as they are employed especially in minimally invasive surgery, preferably in solo surgery as it is called.

BACKGROUND ART

For carrying out complex surgical operations in arthroscopy, a plurality of different instruments and optical equipment are required. Such instruments include so-called active instruments, which are actively employed by the operating surgeon for carrying out surgical measures, and passive or accessory instruments which have the function of enabling the active instruments to be used. Such accessory instruments typically include incision flushing devices, optical devices, and the like.

In clinical use the optical equipment and the accessory instruments are usually held by an assistant and manipulated upon the operating surgeon's request. In order to facilitate or replace the assistant's rather static work, holding arms and support devices for holding the primary surgical instruments during the surgical procedures have been employed in practice and are known from the prior art. The surgical instrument holding devices of the prior art are rather complex and are rather difficult to sterilize prior to use. The holding devices are frequently covered by sterile films during use which further complicates the ability of the surgeon to manipulate them during the surgery.

It would be desirable to provide a relatively uncomplicated and easily sterilized arthroscopic instrument holding device which is sturdy in construction, and can be easily used by the surgeon during the arthroscopy procedure.

DISCLOSURE OF THE INVENTION

This invention relates to a generic instrument holding system which can be easily sterilized, is easy to position, and can stably support and position the surgical trocars in a desired position during the arthroscopic surgery. This invention relies on the fact that internal body cavity walls, for example, the abdominal wall, has a certain intrinsic elasticity which permits a minimum tension to be imparted to the body cavity wall in the direction of the plane of the body cavity wall without the risk of rupturing the body cavity wall. This allows the stationary point of the instrument holding devices to be spaced slightly apart from the patient's body cavity wall so that the entering point of the body cavity wall through which the surgical instruments are inserted is only minimally moved during the surgical procedure due to the instrument lever arm conditions which are established by the holding device. The extent of movement of the tissue at the body cavity entering point does not exceed the extent of movement that would result in shearing of the body cavity wall, thereby avoiding rupture of the body cavity wall during manipulation and positioning of the surgical instruments within the body cavity.

The positioning of the pivotable swivel part of the holding device away from the body cavity wall enables achievement of a considerably simplified design of the instrument holding arm in that the swivel point of the holding arm does not need to be coexistent with the invariable entry point into the body cavity wall, but the swivel point instead can be very close to or located in the area of the holding arm which engages the surgical instrument during use of the system. The system of this invention enable the use of plural holding and instrument position devices to be used during a surgical arthroscopy procedure and enables the surgeon better access to the patient than when a surgical assistant is present. The instrument holding system of this invention also ensures that the adjunct instruments used in performing the surgery will be stably held in place relative the incisions irrespective of the weight of the various adjunct instruments that are needed during the surgery.

The invention will be more readily understood from the following detailed description of several embodiments thereof when taken in conjunction with the accompanying drawings, in which:

DETAILED DESCRIPTION OF THE INVENTION

Figure 1:
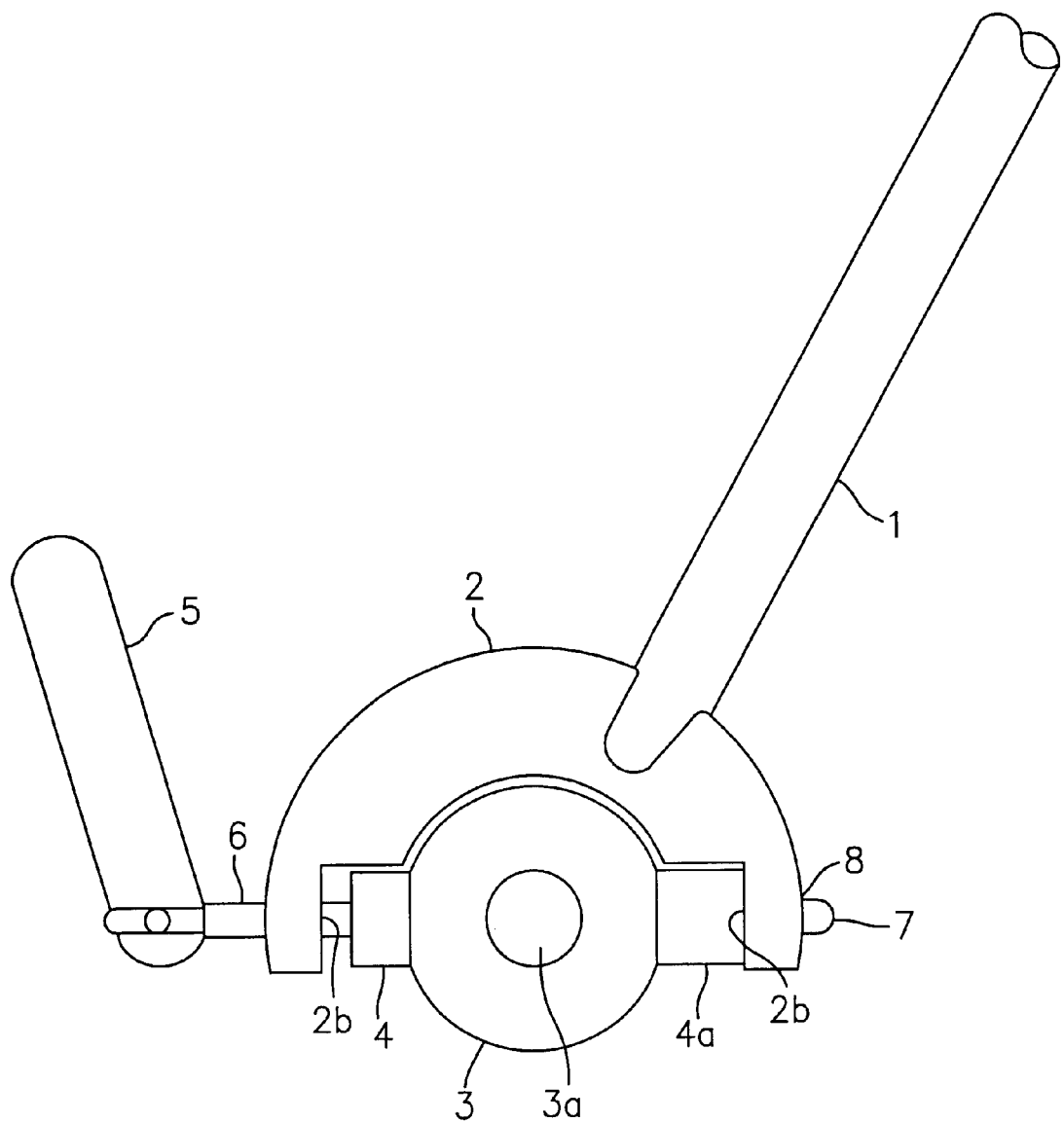
FIG. 1 is an end view of one embodiment of an arthroscopy instrument holding assembly formed in accordance with this invention.
Figure 2:
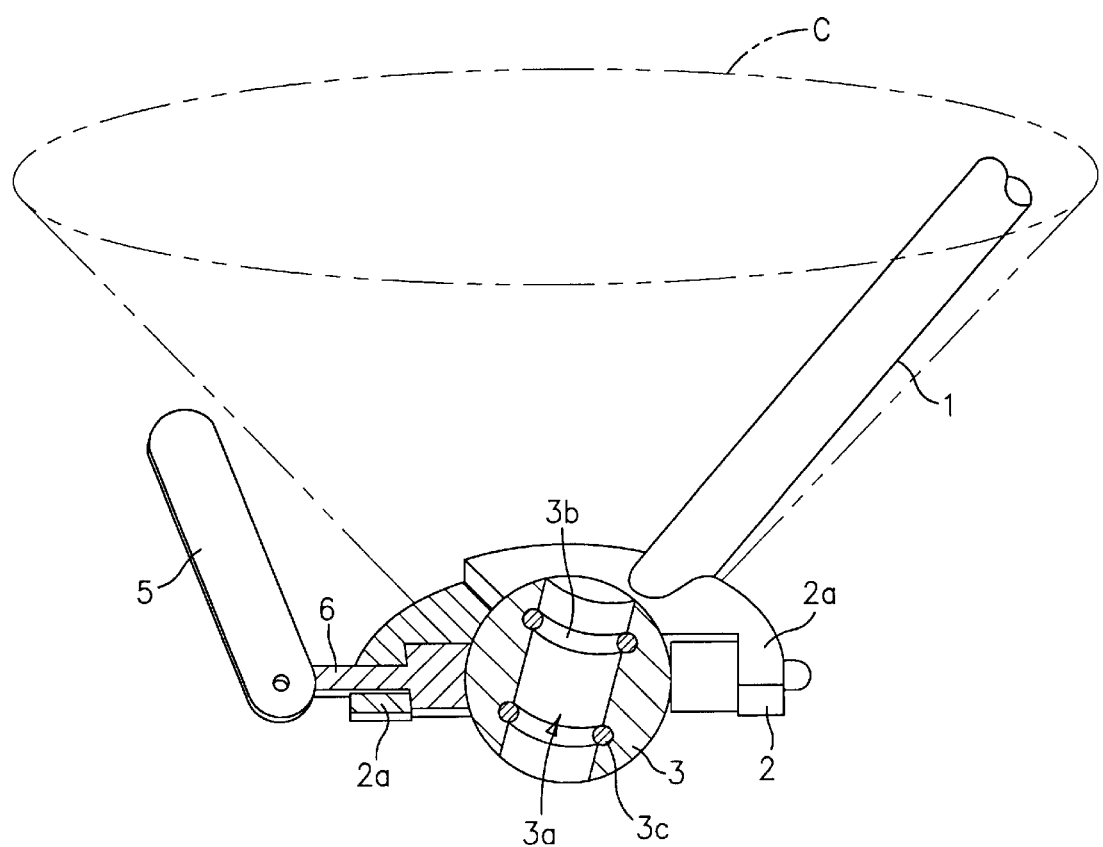
FIG. 2 is a view similar to FIG. 1 showing the degree of possible movement of a trocar which is held in the holding assembly.

Referring now to FIGS. 1 and 2, the holding and positioning device for surgical accessory instruments formed in accordance with this invention comprises a hollow arm 1 which is formed from a metallic or a synthetic material, preferably having specific elastic properties at an end portion thereof where a support frame 2 is firmly affixed thereto. The support frame 2 is a U-shaped yoke having mounting bases 2a at opposite ends thereof. The mounting bases 2a form parallel planar surfaces 2b which are spaced a predetermined distance apart from each other. The mounting bases 2a are penetrated by bores or through holes 2c which are located substantially in the center of the respective mounting bases 2a and are aligned coaxially with each other. In the left-hand bore there is located a support and actuating journal 6 of a first retaining/fixing die 4. The actuating and support journal 6 projects from the outer surface of the support frame 2 and forms a link with one end of an actuating lever 5. The first retaining/fixing die 4 has the form of a cylindrical piston and includes a concave engaging surface 4b in its face that is remote from the support journal 6.

At the opposite mounting base 2a on the right hand side of the yoke 2, there is a second retaining/fixing die 4a which includes a cylindrical piston portion having an inner concave engaging surface 4b and an outer support journal 7 which is positioned in the bore 2c of the die 4a. The journal 7 includes an outer groove in which a retainer snap ring 8 is mounted. Alternatively, the journal 7 could be glued, pressed or otherwise secured in the bore 2c. A receiving ball 3 forms a seat for the surgical instruments. The ball 3 has a central through bore 3a which is located between the two dies 4 and 4a. The ball 3 has a radius which is smaller than the inner radius of the U-shaped support frame 2 so that it is held in position by the two opposed retaining dies 4, 4a. It will be noted from FIG. 1 that the retaining/fixing die 4 can be axially displaced along the journal 6 by the actuating lever 5 as to thereby vary the fixing force applied to the ball 3 to increase the ballclamping force so that the frictional force between the ball surface and the concave faces of the dies 4, 4a so that the ball 3 will be prevented from rotating in the die socket. It should be noted in this context that the one support journal 6 which is coupled with the actuating lever 5 could be a screw which could be tightened and loosened by means of the actuating lever 5. Alternatively, this support journal 6 could be a bolt having a spring surrounding the same which biases the support journal 6 and the integrally formed retaining/fixing die 4 in the direction of the ball 3 with the actuating lever 5 acting, for instance, upon the spring for adjusting the biasing force. In FIG. 2, the arm 1 is shown in a partially broken view seen obliquely from the front.

The ball 3 can be rotated and swiveled within a swivel range between the two dies 4 and 4a, wherein an instrument (not shown) which is inserted through the central ball bore 3a can be moved to various positions which are described by a cone C which is schematically represented in FIG. 2. The swivel point of the ball 3 is located on the center line defined by the two dies 4 and 4a, and is disposed between the two dies 4 and 4a. The ball bore 3a is preferably provided with two axially spaced radial grooves 3b in which elastomeric retaining or packing rings 3c are inserted. These packing rings 3c, by reason of their elasticity, exert a clamping force on an instrument, such as a trocar or the like, which is inserted into the central through bore 3a in the ball 3. In addition, there may be provided a fixing element such as a clamping screw, or the like, which is screwed into the ball and bears against the instrument.

The yoke 2 and the ball 3 combine to form a multi-directionally movable joint mechanism for an instrument which is positioned in the ball bore 3a.

The assembly operates as follows. First, an accessory instrument, for example a trocar, to be employed in the surgery is inserted into the through bore 3a. The instrument is then introduced into the body of a patient to be treated through a body cavity wall of the patient by positioning the ball 3 above the instrument body cavity wall entering point, and then axially moving the instrument through the bore 3a and into the body cavity, in addition to swiveling the instrument into a position within the body cavity desired by the surgeon. The instrument can be manually slid and rotated inside the through bore 3a overcoming the clamping force exerted on the instrument by the packing rings 3c, while the ball 3 can be rotated and swiveled between the two dies 4, 4a. When the accessory instrument is properly positioned, it will be held in place by the packing rings 3c, and also by some additional clamping device such as a damping screw. For finally fixing the accessory instrument in the desired position, the operating surgeon will manipulate the locking lever 5 so as to increase the force applied to the ball 3 by the damping dies 4 and 4a and, in so doing, to clamp the ball 3 against further movement In order to reorient the ball 3 and the instrument connected thereto during the surgical procedure, the surgeon need merely manipulate the lever 5 so as to loosen the clamping force on the ball 3 and then swivel the ball 3 in an appropriate manner. Once the ball 3 is properly repositioned, the lever 5 is manipulated to re damp the ball 3 in its new position. In use during a surgical procedure, the ball 3 will be positioned very dose to, or even in contact with the patient's skin, adjacent to the surgical incision into the body cavity in question. As noted above, the arm 1 preferably can possess a certain intrinsic elasticity so that swiveling movement of the ball 3, and thus the instrument, which is caused by manipulating the arm 1 to swivel the ball 3 will not result in rupturing of the body cavity wall by the instrument due to the elasticity of the arm 1. The degree of elasticity of the arm 1 will be related to the shear strength of the body cavity wall in question.

Figure 2A:
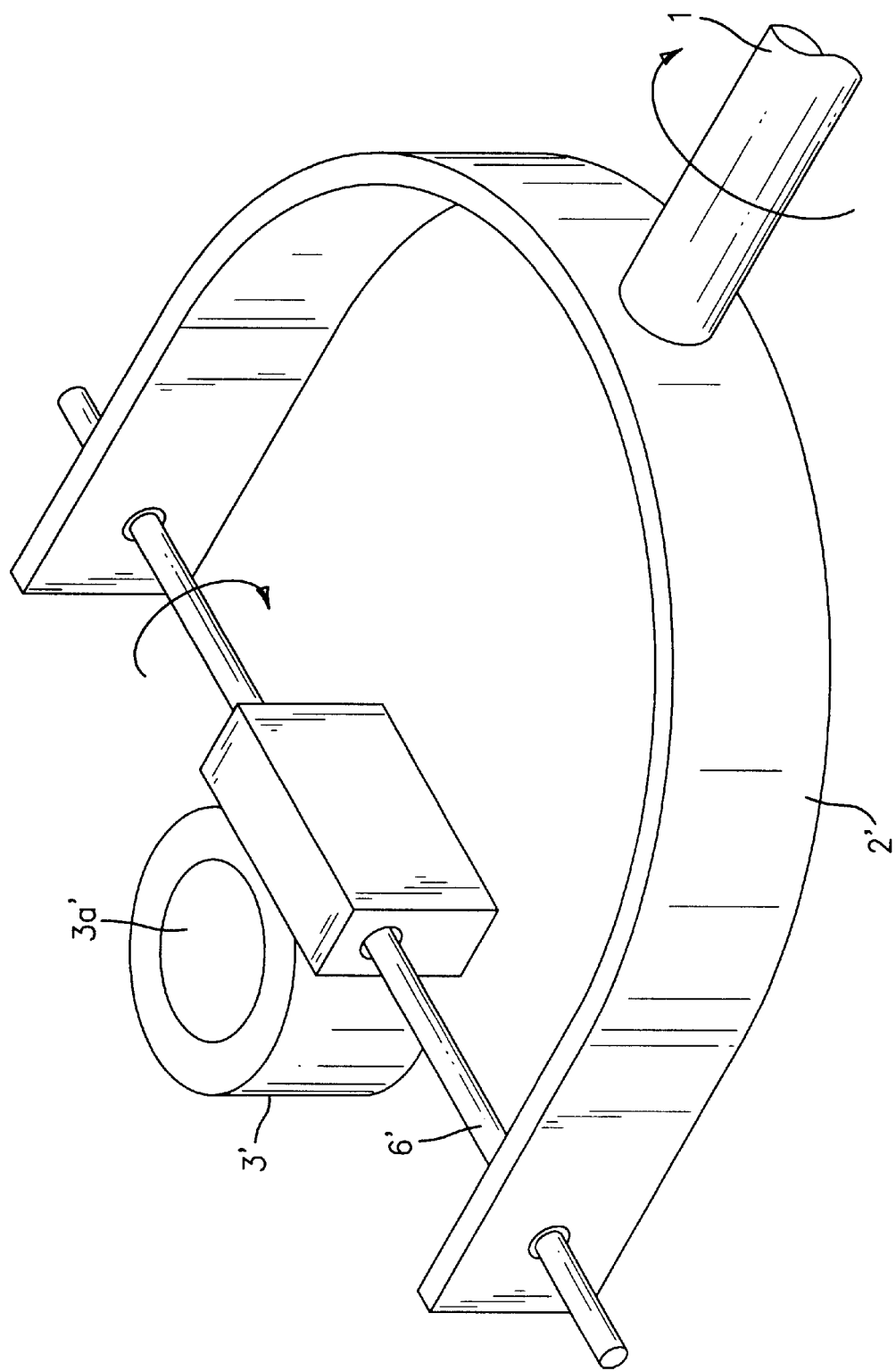
FIG. 2a is a perspective view of another embodiment of an arthroscopy instrument-holding device formed in accordance with this invention.
Figure 2B:
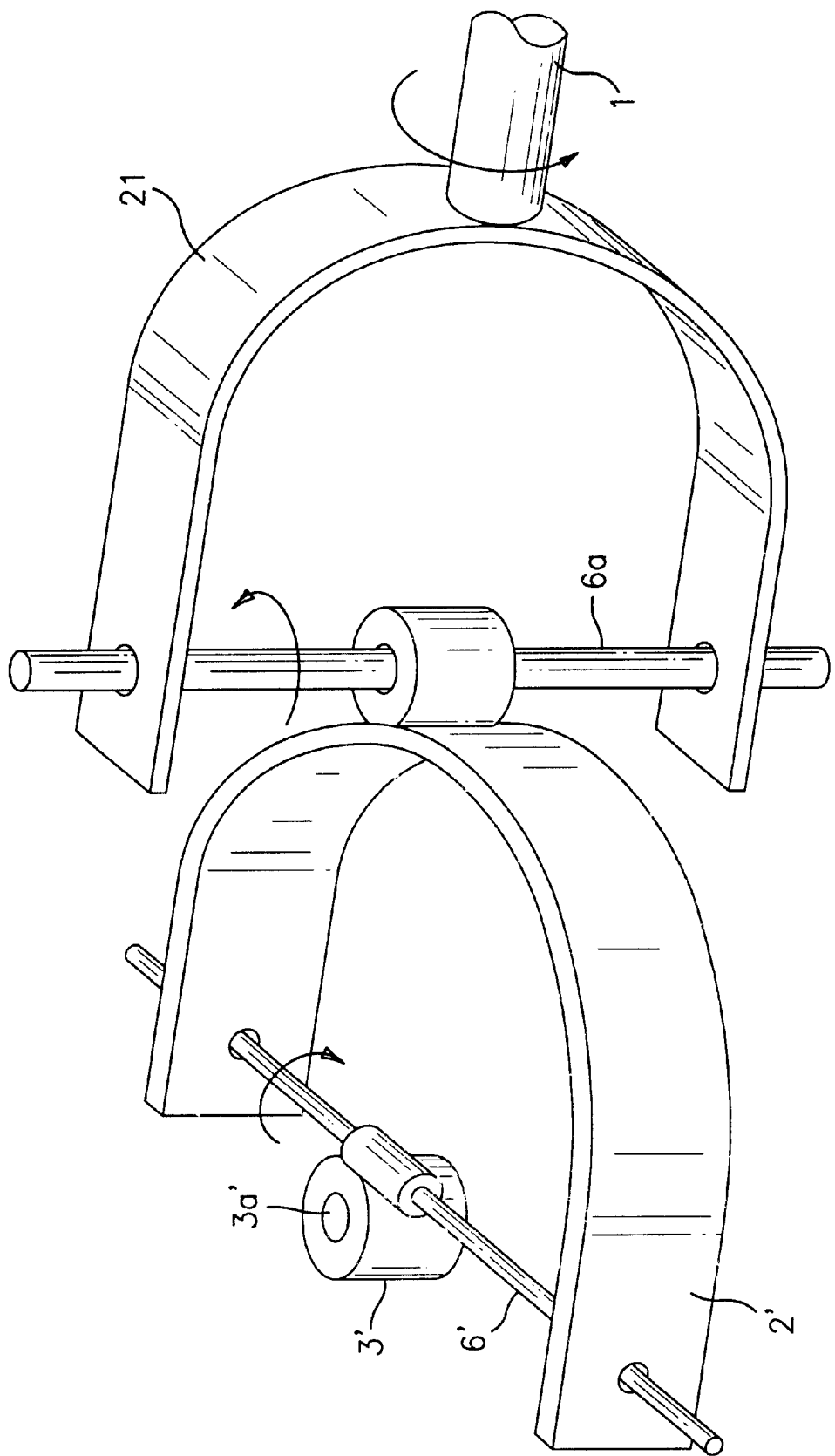
FIG. 2b is a perspective view of yet another embodiment of a holding device formed in accordance with this invention.

Referring now to FIGS. 2a and 2b, there are shown alternative embodiments of mechanisms for holding an auxiliary arthroscopy instrument in place in a body cavity during arthroscopic surgery. Each of the embodiments shown in FIGS. 2a and 2b includes a U-shaped yoke 2' which is rotatable about an arm 1 that is operably connected to the yoke 2'. Each of the embodiments shown in FIGS. 2a and 2b further includes an instrument support member 3' which is pivotable about a support rod 6', and which includes a through passage 3a' pinto which the auxiliary surgical instrument (not shown) is inserted. In the embodiment shown in FIG. 2b, the yoke 2' is further pivotable about a support rod 6a which is mounted in a secondary yoke 21, and is perpendicular to the support rod 6'. In each of the embodiments shown in FIGS. 2a and 2b, the instrument support as member 3' is selectively movable to an operating position so that the instrument can be property positioned in the patient's body cavity during the surgery.

Figure 3:
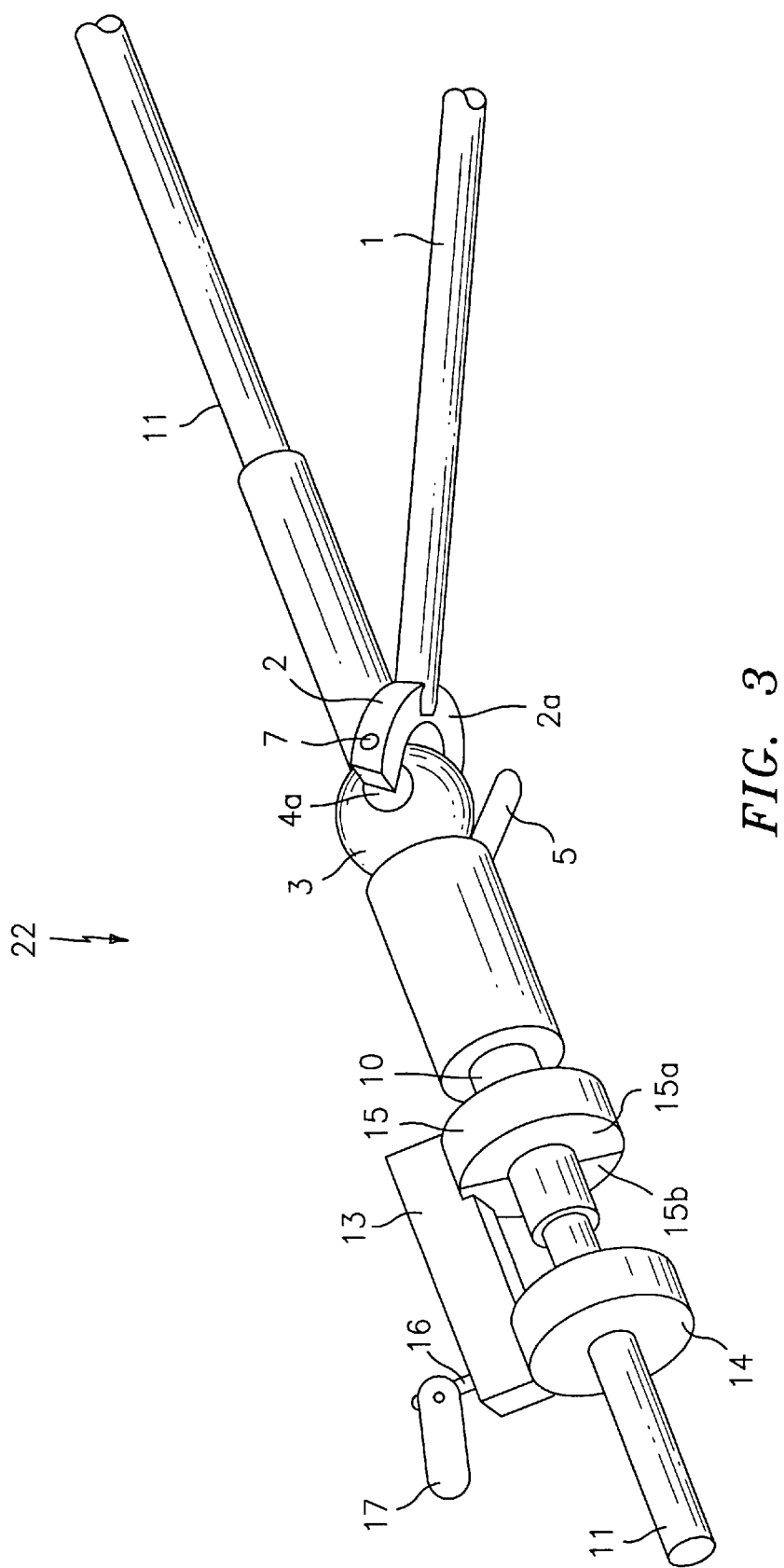
FIG. 3 is a fragmented perspective view of a cluster of the instrument-holding devices formed in accordance with this invention.

Referring now to FIG. 3, there is shown an assembly of the above-described design which includes the system of FIGS. 1 and 2, for fixing an accessory surgical instrument in a trocar 10 that receives the adjunct surgical instrument which can be an optical, or other adjunct surgical instrument 11. The trocar 10 comprises an elongated cylindrical receiving tube into which an adjunct surgical instrument 11 can be inserted. The adjunct surgical instruments 11 to be used are introduced by means of such trocars 10 into the body cavity of a patient being treated. The trocar 10 further has the function of keeping open an access to the body cavity during a change of adjunct instruments 11. The trocars 10 are held in fixed positions relative to the surgical incisions by the holding and positioning devices described above. Once the instrument 11 is properly positioned in the trocar 10 and the body cavity, the instrument 11 will be clamped in place as described hereinafter.

As noted in FIG. 3, an instrument-holding assembly 22 includes a bridge 13 having collars 14 and 15 secured to opposite ends thereof. The collar 15 has a through bore whose diameter substantially corresponds to the outer diameter of the trocar 10 or is slightly larger. The collar 14 is provided with a through bore whose diameter is equal to or slightly larger than the outer diameter of the instrument 11. Preferably the collar 15 is formed with a pair of pivoting opposed jaws 15a and 15b whereby the trocar 10 can be laterally inserted into the through collar bore and the jaws 15a and 15b can be moved toward each other as shown in FIG. 3 to clamp the trocar 10 in place. The two jaws 15a and 15b could also be connected to each other by screws (not shown). The other collar 14 having the through bore which is sized for receiving and guiding the instrument 11 is provided with a clamping screw 16 including an actuating lever 17, which screw 16 is laterally threaded into the collar 14 or above the collar 14 into the bridge 13 and laterally extends into the through bore in the collar 14.

The assembly shown in FIG. 3 operates as follows. First, the collar 15 is clamped onto the trocar 10 prior to introducing the trocar 10 into the body cavity of the patient. It will be understood that the patient is positioned to the right hand side of the assembly as shown in FIG. 3. The trocar 10 is then inserted into the body cavity of the patient. The instrument 11 is then inserted into the trocar 10 and is slid through the trocar 10 and into the patient's body cavity until it reaches the degree of insertion desired by the surgeon. Then the clamping screw 16 is tightened down on the instrument 11 so that the latter is held in place in the trocar 10 in a manner which does not damage the instrument 11. During the insertion operation, the positioning ball 3 will be held in place above the body cavity incision in a manner which is described in greater detail hereinafter.

Figure 4:
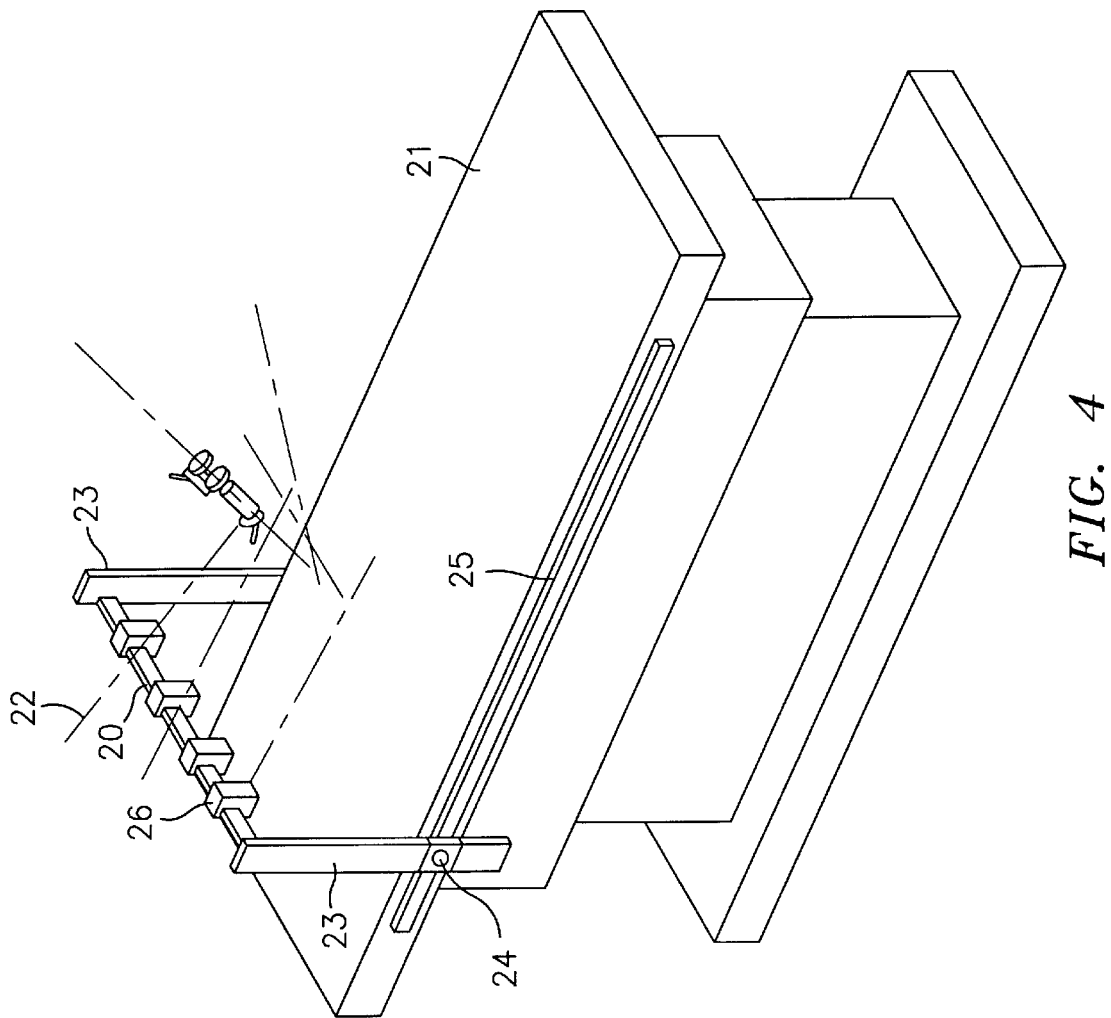
FIG. 4 is perspective view of a surgical operating area which has been equipped with the arthroscopy adjunct instrument positioning and holding system formed in accordance with this invention.
Figure 5:
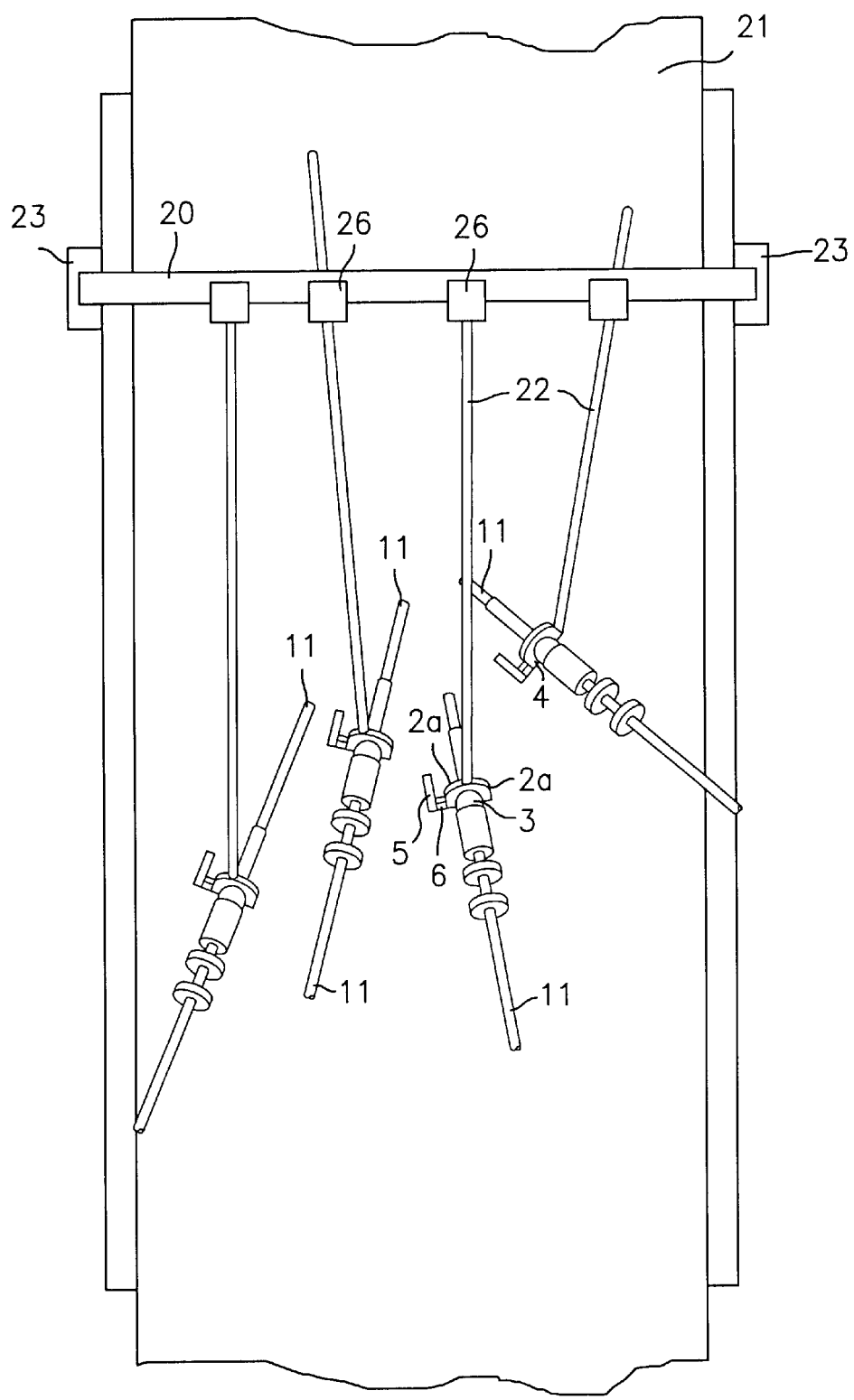
FIG. 5 is a top plan view of the operating area shown in FIG. 4.

Referring now to FIGS. 4 and 5 there is shown a system for positioning the assemblies shown in FIGS. 1, 2 and 3 relative to an operating table 21 during a surgical arthroscopic procedure. A beam 20 is elevated above the operating table 21 by means of one or more supports 23 which are mounted on rails 25 connected to opposite sides of the table 21. The supports 23 are movably connected to the rails 25 by adjustable clamps 24. The length of the supports 23 is such that the beam 20 will be disposed above a patient lying on the table 21. The beam 20 holds clamps 26 which in turn support one or more of the instrument holding assemblies 22 of this invention. FIG. 5 shows how the various instrument holding assemblies 22 can be mounted on the beam 20, and how the balls 3 can be positioned so as to align the various adjunct arthroscopic instruments 11 at various angles relative to a patient positioned on the operating table 21. The clamps 26 can be selectively positioned on the beam 20 as desired by the surgeon.

It will be readily appreciated that the system of this invention allows a surgeon to perform arthroscopic surgery on a patient without the need for attendants who maneuver the adjunct instruments used in the surgery.

Since many changes and variations of the disclosed embodiments of the invention may be made without departing from the inventive concept, it is not intended to limit the invention otherwise than as required by the appended claims.

What is claimed is:

1. A holding and positioning assembly for securing surgical accessory instruments in place during surgery, said assembly comprising a swiveling and rotatable seat for the accessory instruments, said seat including means for gripping the instruments, said seat being linked to a mechanical arm that is manually maneuverable to alter the position of said seat in said assembly via a three dimensionally movable joint mechanism, said joint mechanism including a ball mounted on a support device which is linked to said mehanical arm, said support device comprising a substantially U-shaped frame having opposed legs with coaxial through bores, said through bores containing respective clamps for selectively clamping said ball in a selected pivotal position.

2. The device of claim 1 wherein at least one of said clamps is adjustably movable by means of a handle connected thereto in order to vary the clamping force acting on said ball.

3. The device of claim 1 wherein at least one of said clamps is axially biased by a biasing means.

* * * * *